United States Patent
Roussel et al.

(10) Patent No.: US 8,310,669 B2
(45) Date of Patent: Nov. 13, 2012

(54) SPECTROSCOPIC IMAGING METHOD AND SYSTEM FOR EXPLORING THE SURFACE OF A SAMPLE

(75) Inventors: Bernard Roussel, Valenciennes (FR); Alexandra Rapaport, Hem (FR); Alexandre Kokota, Lille (FR)

(73) Assignee: Horiba Jobin Yvon SAS (FR)

( * ) Notice: Subject to any disclaimer, the term of this patent is extended or adjusted under 35 U.S.C. 154(b) by 464 days.

(21) Appl. No.: 12/596,617

(22) PCT Filed: Apr. 17, 2008

(86) PCT No.: PCT/EP2008/054689
§ 371 (c)(1),
(2), (4) Date: Oct. 19, 2009

(87) PCT Pub. No.: WO2008/128971
PCT Pub. Date: Oct. 30, 2008

(65) Prior Publication Data
US 2010/0134792 A1 Jun. 3, 2010

(30) Foreign Application Priority Data
Apr. 18, 2007 (EP) .................................... 07300962

(51) Int. Cl.
*G01J 3/44* (2006.01)
(52) U.S. Cl. ...................................................... 356/301
(58) Field of Classification Search .................. 356/301, 356/326; 702/189, 199
See application file for complete search history.

(56) References Cited

U.S. PATENT DOCUMENTS

| 5,173,748 A * | 12/1992 | Bilhorn ........................ 356/328 |
| 5,355,165 A | 10/1994 | Kosonocky et al. |
| 5,432,335 A | 7/1995 | West et al. |
| 6,501,861 B1 * | 12/2002 | Cho et al. ...................... 382/243 |
| 6,744,500 B2 * | 6/2004 | Bradbury et al. ............. 356/301 |
| 7,102,746 B2 | 9/2006 | Zhao |
| 2005/0128476 A1 * | 6/2005 | Zhao ............................. 356/301 |
| 2006/0013500 A1 * | 1/2006 | Maier et al. ................... 382/254 |
| 2006/0046311 A1 * | 3/2006 | Sun et al. ...................... 436/518 |

FOREIGN PATENT DOCUMENTS

| EP | 0257379 A2 | 3/1988 |
| EP | 1406304 A2 | 4/2004 |
| WO | 03036271 A2 | 5/2003 |

* cited by examiner

*Primary Examiner* — Kara E Geisel
*Assistant Examiner* — Dominic J Bologna
(74) *Attorney, Agent, or Firm* — Brooks Kushman P.C.

(57) ABSTRACT

A spectroscopic imaging system includes a microscopic or macroscopic device including an objective, a housing including a spectroscope, and scanning means disposed between the objective and the spectroscope. During the scanning of the excitation beam on a scanned area on the sample surface, the energy of the emitted light beam is integrated on the pixels of the detection means, generating average spectral data for each line of pixels. Storage means are connected to the detection means, including a memory able to store average spectral data of M lines of pixels. An imaging device is connected to the storage means, and the average spectral data of M lines of pixels are sent simultaneously toward the imaging device in order to obtain an average spectroscopic image of the scanned area.

12 Claims, 4 Drawing Sheets

SPECTROSCOPIC IMAGING METHOD AND SYSTEM FOR EXPLORING THE SURFACE OF A SAMPLE

BACKGROUND OF THE INVENTION

The invention concerns a spectroscopic imaging method and system for exploring the surface of a sample.

It is particularly useful in Raman spectroscopy. It can equally be used in other forms of spectroscopy such as photoluminescence, fluorescence or cathodoluminescence.

Raman spectroscopy is an analytical technique providing molecule-specific information about a sample. When monochromatic light or radiation strikes a sample, the sample interacts with the light. A portion of the incident radiation may be scattered by the sample. Scattered radiation may contain both an elastic component, in which radiation frequencies remain unchanged, and inelastic components with altered frequencies. Elastically scattered components are called Rayleigh scattering. Inelastic components, if caused by light interacting with the vibrations of molecular bonds, are called Raman scattering.

A prior Raman analysis apparatus is described in a paper "Raman Microprobe and Microscope with Laser Excitation", M Delhaye and P Dhamelincourt, Journal of Raman Spectroscopy, 3 (1975), 33-43 and the document FR 2 253 410. A sample is irradiated with monochromatic light from a laser, and the scattered light is passed through a monochromator in order to select a particular radiation of the resulting Raman spectrum. The monochromator comprises an entrance slit, onto which an optical system of the apparatus focuses an image of an illuminated point or line on the sample. A further optical system focuses an image of the entrance slit onto an exit slit. Between the entrance slit and the exit slit the monochromator has a dispersive device such as a diffraction grating, which has the effect of splitting the incoming Raman spectrum into a range of angles, depending upon frequency. The relative positioning of the exit slit and the diffraction grating thus selects the desired line of interest in the Raman spectrum.

Raman microscopy gained popularity during the last decade because of its capability to analyze microscopic samples down to the size of the sub-µm level. In a Raman microscope, the excitation beam is guided into and the signal beam from an objective lens that serves as focusing and collecting optics.

Another prior art Raman microscope is described in the document U.S. Pat. No. 7,102,746. It discloses a compact Raman spectrometer that may be assembled as an attachment onto infinity corrected light microscope. In order to reduce the size of the spectrometer, this one comprises a laser diode, small optics having small aperture and a CCD detector.

The intensity of a Raman band may be mapped over a two dimensional area or a three dimensional volume of sample by measuring a spectrum on each spot within the sample area or volume, thereby creating a two-dimensional or three dimensional Raman image of sample. Spectral images are useful for visualizing composition distribution on sample. Two dimensional spectral mapping can be done by moving either sample in the X-Y direction, or the laser spot using a pair of galvanometric mirrors with orthogonal scanning axes.

Nevertheless, with classical CCD detectors, the process for transferring the data from the CCD detector to the central unit is slow. One can obtain only few spectra per second even if the energies detected on the pixels have high intensity leading to short exposition times. Spectral data are sent spectrum per spectrum from the CCD detector to the central unit. It needs approximately two hours to obtain a Raman image having a definition of 50 points×50 points. Times required to obtain a Raman image with classical Raman microscope are too important.

BRIEF SUMMARY OF THE INVENTION

One aim of the present invention consists to provide a spectroscopic imaging system for exploring the surface of a sample enabling to reduce times required to obtain a two-dimensional map of a sample surface.

Time required for scanning the sample surface and time required for transferring the data from the CCD detector to the imaging device are significantly reduced.

With such spectroscopic imaging system, it is possible to obtain a Raman image, for example, having a definition of 50 points×50 points, in less than 10 minutes.

Another aim of the present invention consists to provide a spectroscopic imaging method enabling to localize rapidly one or several elements having spectroscopic property at the sample surface, even if the size of the element is in the order of the micrometer.

This spectroscopic imaging method can be generalized and applied for other spectroscopic methods such as photoluminescence, fluorescence, or cathodoluminescence.

To this end, the invention concerns a spectroscopic imaging method for exploring the surface of a sample comprising a first step a) wherein:
  the sample surface is illuminated with an excitation beam, in order to produce an emitted light,
  the emitted light is collected to form an emitted light beam having an energy,
  the energy of the emitted light beam is measured in order to obtain a spectroscopic image of the sample surface.
According to the invention:
  in the first step a), the excitation beam is scanned on the sample surface in two directions X and Y in order to illuminate a scanned area on the sample surface and to measure the energy of the emitted light beam on the scanned area, the energy of the emitted light beam being integrated during the scanning of the excitation beam on the scanned area and a time t, in order to obtain an average spectroscopic image of the scanned area,
  the spectroscopic imaging method further comprises:
    a second step b) wherein the preceding first step a) is repeated for one or several other scanned areas of the sample surface, each scanned area being contiguous to at least one other scanned area,
    a third step c) wherein one or several information are selected in the measured energy,
    a fourth step d) wherein one or more scanned areas are divided in several smaller scanned areas if at least a selected information is detected in said scanned areas,
  the preceding steps a) to d) are applied to at least a smaller divided scanned area.

This spectroscopic imaging method enables to localize quickly one or several elements on the sample surface. Sample areas where no information is detected, are not processed. The process is limited to the sample areas comprising one or more characteristic information of the one or several searched elements. It is possible to localize quickly the elements with a high precision. One obtains a two-dimensional map wherein all the searched and interesting elements are localized, in less than 10 minutes.

According to various embodiments, the present invention also concerns the characteristics below, considered individually or in all their technical possible combinations:

the energy of the emitted light beam is measured with a detection means comprising several vertical lines of pixels and several horizontal lines of pixels, one of the horizontal line of pixels being a reading line, each line of pixels including several pixels, and the operation of measurement of the first step a) comprising the steps of:

e) polarizing the pixels of at least one horizontal line of pixels receiving the integrated energy of the emitted light beam during the time t, generating an amount of electric charges accumulated in each pixel of the at least one horizontal line of pixels, f) transferring simultaneously the amount of electric charges of all the pixels of the polarized horizontal line of pixels toward the reading line, g) transferring the amount of electric charges of each pixel of the reading line toward an electronic device, said electronic device being able to convert each amount of electric charges into a voltage value, the steps f) and g) are controlled by a storage means comprising a control means, said storage means controlling the transfer rate of the amount of electric charges of the pixels, after the step g) the tension value of each pixel of the reading line is stored in the storage means, said storage means being able to store an amount of tension values corresponding to M horizontal lines of pixels, and said stored amount of voltage values corresponding to M horizontal lines of pixels is sent toward an imaging device in order to obtain an average spectroscopic image of the scanned area.

The present invention permits reducing the times required for data transfer between the detection means and the imaging device as well as increasing the data rate. The data rate is the speed of a data transfer process, normally expressed in Hz.

Up to 250 spectra can be stored in the storage means and be simultaneously send to the imaging device. The method according to the invention permits to process (acquisition step+data transfer) up to 250 spectra per second.

during the second step b), the first step a) is applied to four scanned areas of the sample surface, said four scanned areas being contiguous, during the fourth step d), at least one of the four scanned areas is divided in four smaller scanned areas if at least a selected information is detected in said at least one of the four scanned areas, the preceding steps a) to d) are applied to the four smaller divided scanned areas, the steps a) to g) are automatically realized, the step a), the scanned area is continuously scanned by the excitation beam, the spectroscopic imaging method for exploring the surface of a sample is a Raman imaging method for exploring the surface of a sample having Raman property, said excitation beam being a monochromatic light beam able to produce a Raman scattered light, said Raman scattered light being collected to form a Raman scattered light beam having an energy and said energy being filtered and measured in order to obtain a Raman image of the sample surface.

The present invention also concerns a spectroscopic imaging system for exploring the surface of a sample comprising:

a microscopic or macroscopic device including an objective, a housing including a spectroscope, said spectroscope comprising:

an excitation source able to generate an excitation beam incident to the sample surface, producing an emitted light, collecting means able to collect the emitted light to form an emitted light beam having an energy, detection means able to measure the energy of the emitted light beam in order to obtain a spectroscopic image of the sample surface, said detection means comprising at least one line of pixels, scanning means disposed between the objective of the microscopic or macroscopic device and the spectroscope, said scanning means being disposed in the optical path of the excitation beam and being able to scan the sample surface in two directions X and Y in order to illuminate a scanned area on the sample surface.

According to the invention:

during the scanning of the excitation beam on the scanned area, the energy of the emitted light beam measured on the scanned area is integrated on the pixels of said lines of pixels of the detection means, generating average spectral data for each line of pixels, storage means are connected to the detection means, said average spectral data of each line of pixels being transferred toward the storage means, and said storage means comprising a memory able to store average spectral data of M lines of pixels, and an imaging device is connected to the storage means, said average spectral data of M lines of pixels being send simultaneously toward said imaging device in order to obtain an average spectroscopic image of the scanned area.

According to various embodiments, the present invention also concerns the characteristics below, considered individually or in all their technical possible combinations:

the storage means comprises control means for controlling the transfer rate of the average spectral data of the pixels of the lines, the storage means is a Field Programmable Gate Array module (FPGA), the spectroscope is an attachment for the microscopic or macroscopic device, the housing including said spectroscope being insertable into said microscopic or macroscopic device and extractable from this one, the scanning means comprise two galvanometric mirrors, the spectroscopic imaging system for exploring the surface of a sample is a Raman imaging system for exploring the surface of a sample having Raman property, said spectroscope being a Raman spectroscope comprising:

a monochromatic light source able to illuminate the sample surface with a monochromatic light beam, in order to produce a Raman scattered light, a collecting means able to collect the Raman scattered light to form a Raman scattered light beam having an energy, and filtering means and detection means able to filter and measure the energy of the Raman scattered light beam in order to obtain a Raman image of the sample surface.

The association of the scanning means with the storage means of the detection means enables to obtain a spectral image such as a Raman image in less than 10 minutes, with a good precision (50 points×50 points). Time required to obtain a spectral image is significantly reduced. The using of scanning means such as galvanometric mirrors permits to reduce the time t required to scan the sample surface. And the using of storage means such as FPGA permits to reduce the time required for transferring the data from the detector to the FPGA and the time required for transferring the data from the FPGA to the imaging device.

This spectroscopic imaging system is particularly useful when applied to the above described spectroscopic imaging method for localizing an element on a sample surface. One can visualize all the interesting elements of the sample surface on a two-dimensional map, in less than 10 minutes.

BRIEF DESCRIPTION OF THE DRAWINGS

The description of the invention is illustrated by the following drawings in which.

DETAILED DESCRIPTION OF THE INVENTION

Figure 1:
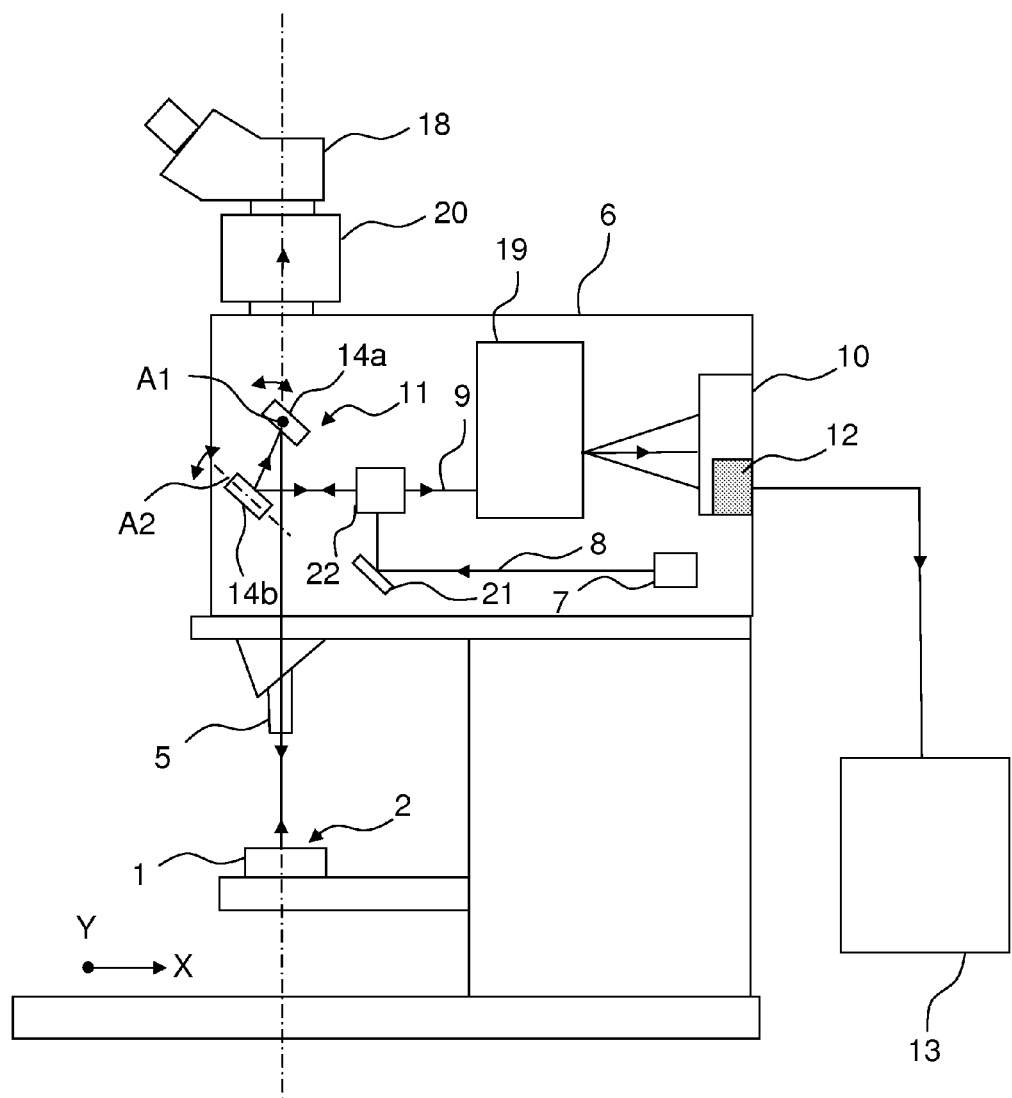
FIG. 1 is a schematic representation of a spectroscopic imaging system, according to one embodiment of the invention.

FIG. 1 is a schematic representation of a spectroscopic imaging system for exploring the surface 2 of a sample 1, according to one embodiment of the invention.

The spectroscopic imaging system comprises a microscopic or macroscopic device which can be an infinity corrected microscope, as described in the document U.S. Pat. No. 7,102,746.

In infinity corrected microscopes, visible light gathered from a sample 1, is collimated by an objective 5 which can be a lens, and is formed into an image by a tube lens (not shown), usually located within a viewing device 18. Because light is collimated between the objective 5 and the tube lens, many components may be inserted in this region without substantially affecting imaging quality.

The spectroscopic imaging system comprises a housing 6 including a spectroscope. The housing 6 of the spectroscopic imaging system can be definitely fixed to the microscopic or macroscopic device in a not movable manner. Alternatively, the spectroscope can be an attachment for the microscopic or macroscopic device. The housing 6 including the spectroscope is insertable into the microscopic or macroscopic device and is extractable from this one.

The spectroscope comprises an excitation source 7 generating an excitation beam 8, incident to the sample surface 2, producing an emitted light.

It can comprise filtering means 22 mounted in the path of the excitation beam 8 for directing the excitation beam 8 toward the objective 5 of the microscopic or macroscopic device. Filtering means 22 is selected from the group of dichroïc mirrors, mirrors provided with one or several holes, holographic filters, interference filters and beam splitters.

It comprises collecting means able to collect the emitted light to form an emitted light beam 9 having an energy. The collecting means of the spectroscope can include the objective 5 of the microscopic or macroscopic device. In a preferred embodiment of the invention, the excitation beam 8 and the emitted light beam 9 are combined into a common optical path. Filtering means 22 redirect the emitted light beam 9 toward the spectroscope.

In another possible embodiment of the invention, the excitation beam 8 and the emitted light beam 9 are not combined into a common optical path.

The spectroscope can comprise spectroscopic means 19 such as dispersing means, slits, Notch filters and mirrors.

The spectroscope comprises detection means 10 able to measure the energy of the emitted light beam 9 in order to obtain a spectroscopic image of the sample surface 2. The detection means 10 can be a CCD detector comprising at least one line of pixels.

The operations of illumination of the sample surface 2 with the excitation beam 8, collection of the emitted light, and measurement of the energy of the emitted light beam 9 are included in a first step a) of the spectroscopic imaging method.

CCD detectors or image sensors (charge coupled device) are electronic devices that are capable of transforming a light pattern (image) into an electric charge pattern (an electronic image). The CCD consists of several individual elements that have the capability of collecting, storing and transporting electrical charge from one element to another. This together with the photosensitive properties of silicon, is used to design image sensors. Each photosensitive element represent a picture element (pixel). With semiconductor technologies and design rules, structures are made that form lines, or matrices of pixels. An electronic device 17 comprising one or more output amplifiers at the edge of the chip collects the signals from the CCD detector. An electronic image can be obtained by, after having exposed the sensor with a light pattern, applying series of pulses that transfer the charge of one pixel after another to the electronic device 17, line after line. The electronic device 17 converts the charge into a voltage. External electronics will transform this output signal into a form suitable for monitors or frame grabbers. CCD detectors have extremely low noise figures.

The spectroscopic imaging system comprises a scanning means 11 disposed between the objective 5 of the microscopic or macroscopic device and the filtering means 22. The scanning means 11 is disposed in the optical path of the excitation beam 8 and permits to scan spatially the sample surface 2 in two directions X and Y in order to illuminate a scanned area 3 on the sample surface 2. The scanning means 11 is preferably included in the housing 6 of the spectroscopic imaging system. It can be included in a different housing.

In a preferred embodiment, the scanned areas 3 have a quadrilateral shape but can have a circular shape or an ellipsometric shape or another shape. In a more preferred embodiment, the scanned areas 3 have approximately a square shape.

The scanning means 11 can comprise a first galvanometric mirror 14a and a second galvanometric minor 14b with respective orthogonal scanning axes A1, A2. In the example of FIG. 1, the orthogonal scanning axes A1 of the first galvanometric mirror 14a is parallel to the plan (X,Y) and perpendicular to the optical path between the sample 1 and the first galvanometric minor 14a. In other words, the orthogonal scanning axes A1 of the first galvanometric minor 14a is perpendicular to the plan of the sheet comprising the FIG. 1. The rotation of the first galvanometric mirror 14a allows the scanning of the sample surface 2 according to the direction X. The orthogonal scanning axes A2 of the second galvanometric minor 14b is inclined with respect to the plan (X, Y) and parallel to the plan of the sheet comprising the FIG. 1. The rotation of the second galvanometric mirror 14b allows the scanning of the sample surface 2 according to the direction Y.

The scanned area 3 can be scanned continuously or step by step by the excitation beam 8.

The scanning means 11 can be removed to permit ordinary use of the microscopic or macroscopic device, e.g. to permit setting-up and ordinary optical examination of the sample 1. For these purposes, the microscopic or macroscopic device can comprise a light source 20 of white light above the location of the scanning means 11 for illuminating the sample 1. In an alternative embodiment, the scanning means 11 can be positioned above the light source 20.

In the embodiment wherein the spectroscope is an attachment for the microscopic or macroscopic device, the housing 6 including the spectroscope can be extractable from the microscopic or macroscopic device in order to permit ordinary use of the microscopic or macroscopic device.

In the example of FIG. 1, the excitation beam 8 is sent toward a minor 21 that reflects the excitation beam 8. The reflected excitation beam 8 is directed to the filtering means 22 which transmits the excitation beam 8 to the second galvanometric minor 14*b*. After being reflected on the second galvanometric minor 14*b*, the excitation beam 8 is also reflected on the first galvanometric minor 14*a* and directed toward the sample surface 2 passing through the objective 5 of the microscopic or macroscopic device.

The excitation beam 8 is incident to the sample surface 2 and reflected on or scattered by the sample surface 2, producing an emitted light (scattered light in the case of Raman spectroscopy). A part of the emitted light is collected by the objective 5 of the microscopic or macroscopic device, generating an emitted light beam 9 directed toward the first galvanometric mirror 14*a*. The emitted light beam 9 is directed toward the filtering means 22 and then to the spectroscopic means 19 of the spectroscopic imaging system. The energy of the emitted light beam 9 is then measured by the detection means 10 generating a spectroscopic image of the sample surface 2.

According to one embodiment of the invention, during the scanning of the excitation beam 8 on the scanned area 3 in the two directions X, Y, the energy of the emitted light beam 9 measured on the scanned area 3 is integrated on the pixels of one or more pixels lines of the detection means 10, generating average spectral data for the pixels lines. Average spectral data are representative of an average spectrum. The average spectrum of the scanned area 3 is recorded and integrated by the detection means 10 during a time t. Time t represents an integration period. The time t is in the order of the second.

Figure 4:
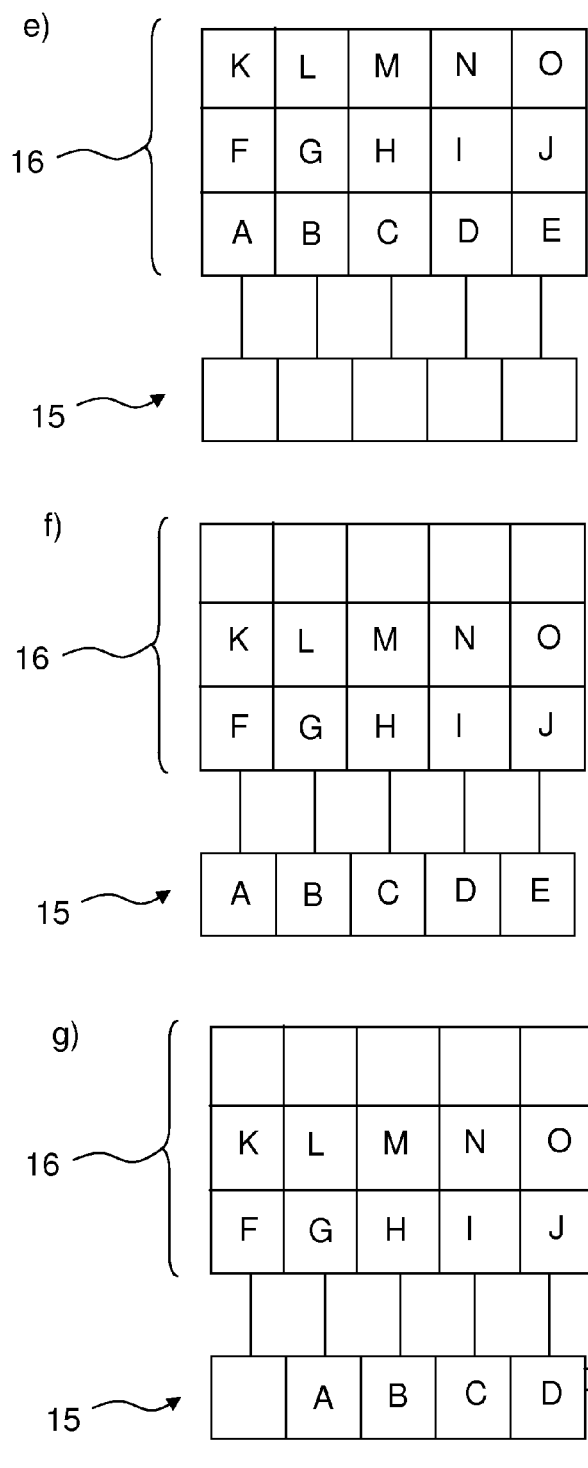
FIG. 4 is a schematic representation of an operation of measurement of the spectroscopic imaging method, according to one embodiment of the invention.

The detection means 10 comprises several vertical lines of pixels and several horizontal lines of pixels, forming a matrix 16 of pixels, as illustrated in FIG. 4. One of the horizontal lines of pixels is a reading line 15. Each line of pixels includes several pixels.

FIG. 4 is a schematic representation of an operation of measurement of the spectroscopic imaging method. In this example, the detection means 10 which is a CCD detector comprises four horizontal lines of pixels and five vertical lines of pixels. The detection means 10 can comprise more or less lines of pixels.

The operation of measurement of the first step a) of the spectroscopic imaging method comprises the steps of:
 e) polarizing the pixels of at least one horizontal line of pixels receiving the integrated energy of the emitted light beam 9 during the time t, generating an amount of electric charges accumulated in each pixel of the at least one horizontal line of pixels,
 f) transferring simultaneously the amount of electric charges of all the pixels of the polarized horizontal line of pixels toward the reading line 15,
 g) transferring the amount of electric charges of each pixel of the reading line 15 toward the electronic device 17.

The electronic device 17 converts each amount of electric charge into a voltage value.

With classical CCD detectors, the above described process is slow. One can obtain only a few spectra per second even if the energies detected on the pixels have high intensity leading to short exposure times. This process leads to a bottleneck at the input of the electronic device 17.

To overcome this drawback, the spectroscopic imaging system comprises a storage means 12 connected to the detection means 10. The storage means 12 can or not be integrated in the housing 6 of the spectroscopic imaging system.

The average spectral data of each line of pixels are transferred toward the storage means 12. The storage means 12 comprises a memory able to store an amount of tension values corresponding to M horizontal lines of pixels. In one possible embodiment each spectrum of a scanned area 3 is recorded on a horizontal line of pixels (one horizontal line of pixels per spectrum). M may be between 50 to 250 lines of pixels. M is preferably equal to 250 lines of pixels. Alternatively, a spectrum can be measured on a matrix of pixels. After the step g), the tension value of each pixel of the reading line 15 is stored in the storage means 12.

An imaging device 13 is connected to the storage means 12. The imaging device 13 can be a central unit connected to a monitor. The stored tension values corresponding to M horizontal lines of pixels are sent simultaneously to the imaging device 13. It permits to reduce the times required for data transfer between the detection means 10 and the imaging device 13 and to increase the data rate. Classically, spectral data are sent spectrum per spectrum from the detection means 10 to the imaging device 13 leading to long times of data transfer.

According to a possible embodiment of the invention, the steps f) and g) are controlled by the storage means 12 which comprises a control means. The control means of the storage means 12 controls the transfer rate of the amount of electric charges of the pixels. To this end, the control means of the storage means 12 comprises a first clock CLK1 and a second clock CLK2.

The first clock CLK1 controls the step f) of transferring simultaneously the amount of electric charges of all the pixels of the polarized horizontal line of pixels toward the reading line 15. During a clock cycle, the electric charges of all the pixels of a polarized horizontal line of pixels is transferred toward the reading line 15. To this end, the control means of the storage means 12 send a pulse to the detection means 10. The frequency of the first clock CLK1 is approximately equal to 9 µs/line.

The second clock CLK2 controls the step g) of transferring the amount of electric charges of each pixel of the reading line 15 toward the electronic device 17. During a clock cycle, an electric charge of one pixel of the reading line 15 is transferred toward the electronic device 17. To this end, the control means of the storage means 12 sends a pulse to the detection means 10. The frequency of the second clock CLK2 is approximately equal to 1 µs/pixel.

The storage means 12 can be a Field Programmable Gate Array module (FPGA). A FPGA is a semiconductor device containing programmable logic components and programmable interconnects. The programmable logic components can be programmed to duplicate the functionality of basic logic gates such as AND, OR, XOR, NOT or more complex combinational functions such as decoders or simple math functions. In most FPGAs, these programmable logic components (or logic blocks) also include memory elements, which may be simple flip-flops or more complete blocks of memories. FPGA contains an array of logic cells surrounded by programmable I/O blocks. It can contain as many as tens of thousands of logic cells and an even greater number of flip-flops. The FPGA can run with a clock rate of sub-500 MHz.

Alternatively, the storage means 12 can be another programmable device such as a complex programmable logic device (CPLD).

The storage means 12 permits to accelerate the operation of measurement of the spectroscopic imaging system. It controls directly the transfer of the electric charges in the CCD detector.

The storage means 12 is advantageously positioned in the head of the CCD detector, in the vicinity of the CCD detector chip. It permits to limit the noise due to high speed operations. The spectroscopic imaging system can process up to 250 spectra per second.

In a particular embodiment, the spectroscopic imaging system for exploring the surface 2 of a sample 1 is a Raman imaging system and the sample surface 2 has Raman property. The spectroscope is a Raman spectroscope. The excitation source 7 is a monochromatic light source 7 able to illuminate the sample surface 2 with a monochromatic light beam 8, in order to produce a Raman scattered light.

The Raman spectroscope comprises collecting means able to collect the Raman scattered light to form a Raman scattered light beam 9 having an energy. Collecting means can comprise the objective 5 of the microscopic or macroscopic device.

The Raman spectroscope comprises a spectroscopic device 19 which can comprise means for dispersing the scattered light beam 9, such as a dispersion grating (not represented). It can comprise selection means not represented, such as a slit for example, able to select the energy of the Raman scattered light beam 9. It can comprise filtering means (not represented), such as a Notch filter, able to filter the energy of the Raman scattered light beam 9. Notch filter permits to reject the Rayleigh radiation of the scattered light beam 9.

The Raman spectroscope comprises detection means 10 able to measure the energy of the Raman scattered light beam 9 in order to obtain a Raman image of the sample surface. The detection means 10 of the Raman spectroscope is a CCD detector.

Alternatively, the spectroscopic imaging system for exploring the surface 2 of a sample 1 can be a photoluminescence imaging system or a fluorescence imaging system or a cathodoluminescence imaging system.

In the embodiment wherein the spectroscopic imaging system is a cathodoluminescence imaging system, the scanning means 11 consist in a pair of deflectors having respectively two perpendicular rotation axis. The sample surface 2 is sputtered with an electron beam, producing an emitted light. The emitted light is collected by the objective 5 of the microscopic or macroscopic device to form an emitted light beam 9 having an energy.

The path of the electron beam is different from the optical path of the emitted light beam 9 which passes through the objective 5.

In the other above cited embodiments, the optical path of the excitation light beam 8 is identical to the optical path of the emitted light beam 9, between the sample surface 2 and the second galvanometric mirror 14b.

The invention also concerns a spectroscopic imaging method for exploring the surface 2 of a sample 1 comprising the above described first step a wherein the sample surface 2 is illuminated with the excitation beam 8, in order to produce an emitted light. The emitted light is then collected to form an emitted light beam 9 having an energy. And the energy of the emitted light beam 9 is measured in order to obtain a spectroscopic image of the sample surface 2.

Figure 2:
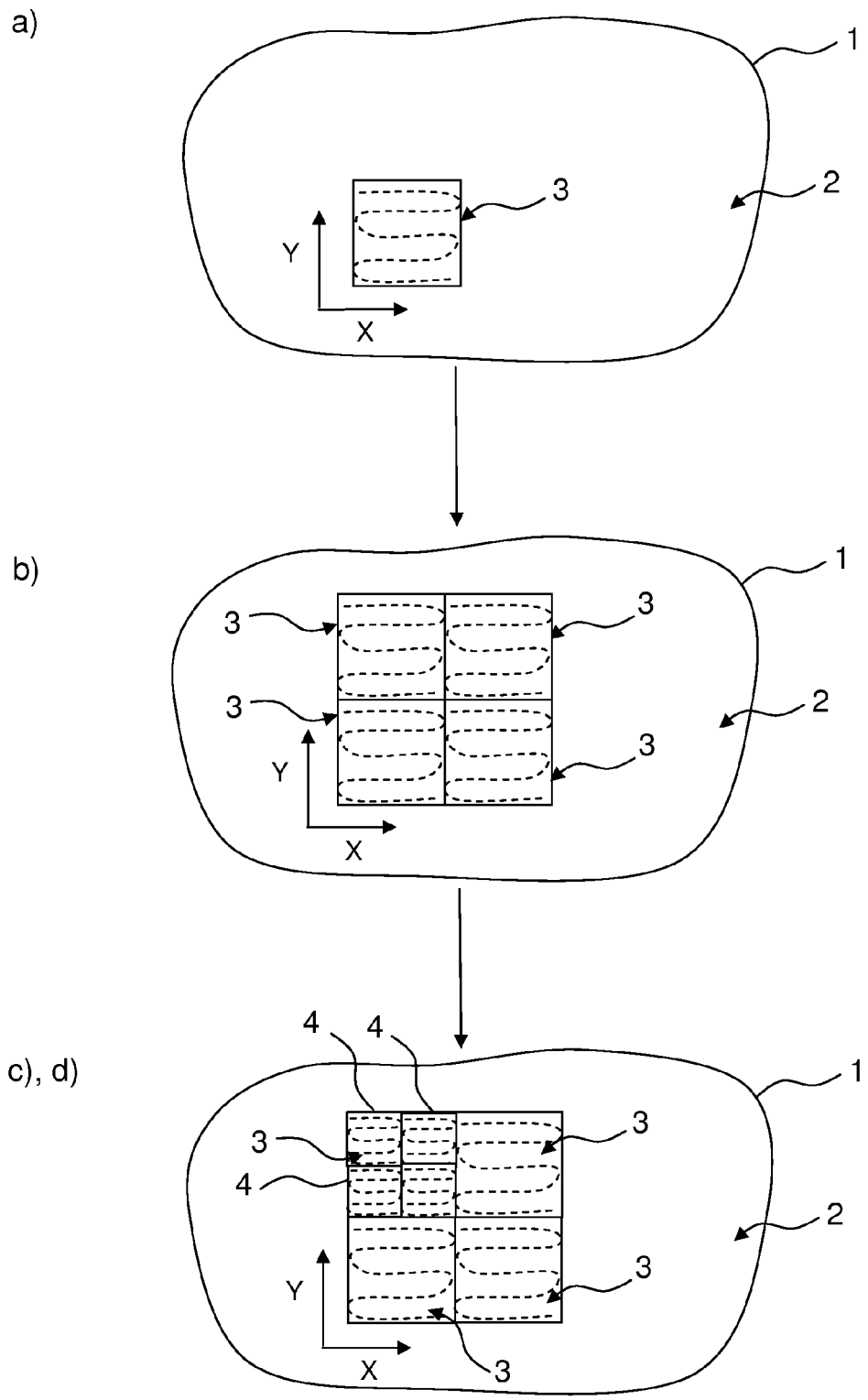
FIG. 2 is a schematic representation of a spectroscopic imaging method, according to one embodiment of the invention.

According to a possible embodiment of the invention, represented in FIG. 2, in the first step a), the excitation beam 8 is scanned on the sample surface 2 in two directions X and Y in order to illuminate a scanned area 3 on the sample surface 2 and to measure the energy of the emitted light beam 9 on the scanned area 3. The energy of the emitted light beam 9 is integrated during the scanning of the excitation beam 8 on the scanned area 3, corresponding to the time t (integration period), in order to obtain an average spectroscopic image of the scanned area 3. The time t is in the order of the second.

The spectroscopic imaging method further comprises a second step b) wherein the preceding first step a) is repeated for one or several other scanned areas 3 of the sample surface 2. Each scanned area 3 is contiguous to at least one other scanned area 3.

The spectroscopic imaging method also comprises a third step c) wherein one or several information are selected in the measured energy and a fourth step d) wherein one or more scanned areas 3 are divided in several smaller scanned areas 4 if at least a piece of selected information is detected in the scanned areas 3. For instance, the selected information can be spectral information such as a spectral band or a wavelength. For example, the selected information can consist in a wavelength of a first searched element and a wavelength of a second searched element. The selected information is characteristic of one or several elements which are intended to be localized on the sample surface 2.

The preceding steps a) to d) are applied to at least a smaller divided scanned area 4. The preceding steps a) to d) can be repeated until the desired resolution is reached.

This spectroscopic imaging method enables to localize quickly one or several elements on the sample surface 2. The sample areas comprising no information, are not processed. The process is limited to the sample areas comprising one or more characteristic information of the one or several searched elements. It is possible to localize quickly the elements with a high precision and resolution. One obtains a two-dimensional map wherein all the searched elements are localized in less than 10 minutes.

This method is particularly efficient when using the above described spectroscopic imaging system comprising storage means 12 and scanning means 11.

In the particular embodiment of FIG. 2, during the second step b), the first step a) is applied to four scanned areas 3 of the sample surface 2. The four scanned areas 3 are contiguous.

Two scanned areas 3 are selected in the direction X and two scanned areas 3 are selected in the direction Y. More precisely, two points are selected in the direction X and two points are selected in the direction Y. Each selected point is approximately localized in the centre of the respective scanned areas 3.

The excitation beam 8 can be scanned at a distance of +/−12.5 μm around each selected point of the sample surface 2, in the two directions X and Y. One obtains an image of four scanned areas 3 having each a surface of 25 μm×25 μm.

One determinates if one of the four scanned areas 3 contains at least an information characteristic of the one or several elements intended to be localized.

If one of the four scanned areas 3 contains the above cited information, this one is divided in four smaller scanned areas 4, two smaller scanned areas 4 in the direction X and two smaller scanned areas 4 in the direction Y.

The excitation beam 8 can be scanned at a distance of +/−6.25 μm around a point localized in the centre of each smaller scanned area 4, in the two directions X and Y. One obtains an image of four smaller scanned areas 4 having each a surface of 12.5 µm×12.5 µm.

One determinates if one of the four smaller scanned areas 4 contains an information characteristic of the one or several elements intended to be localized.

The preceding operations are repeated for one or more smaller scanned areas 4, if it contains the information characteristic of the one or several elements intended to be localized.

The process is stopped when the wished precision is reached or when no information is found after the second step b).

The scanned areas 3 containing the information characteristic of the one or several elements intended to be localized, can be divided in more or less than four smaller scanned areas 4. The number of divisions can vary during the process.

The steps a) to g) of the spectroscopic imaging method for localizing an element can be automatically or manually realized.

Figure 3:
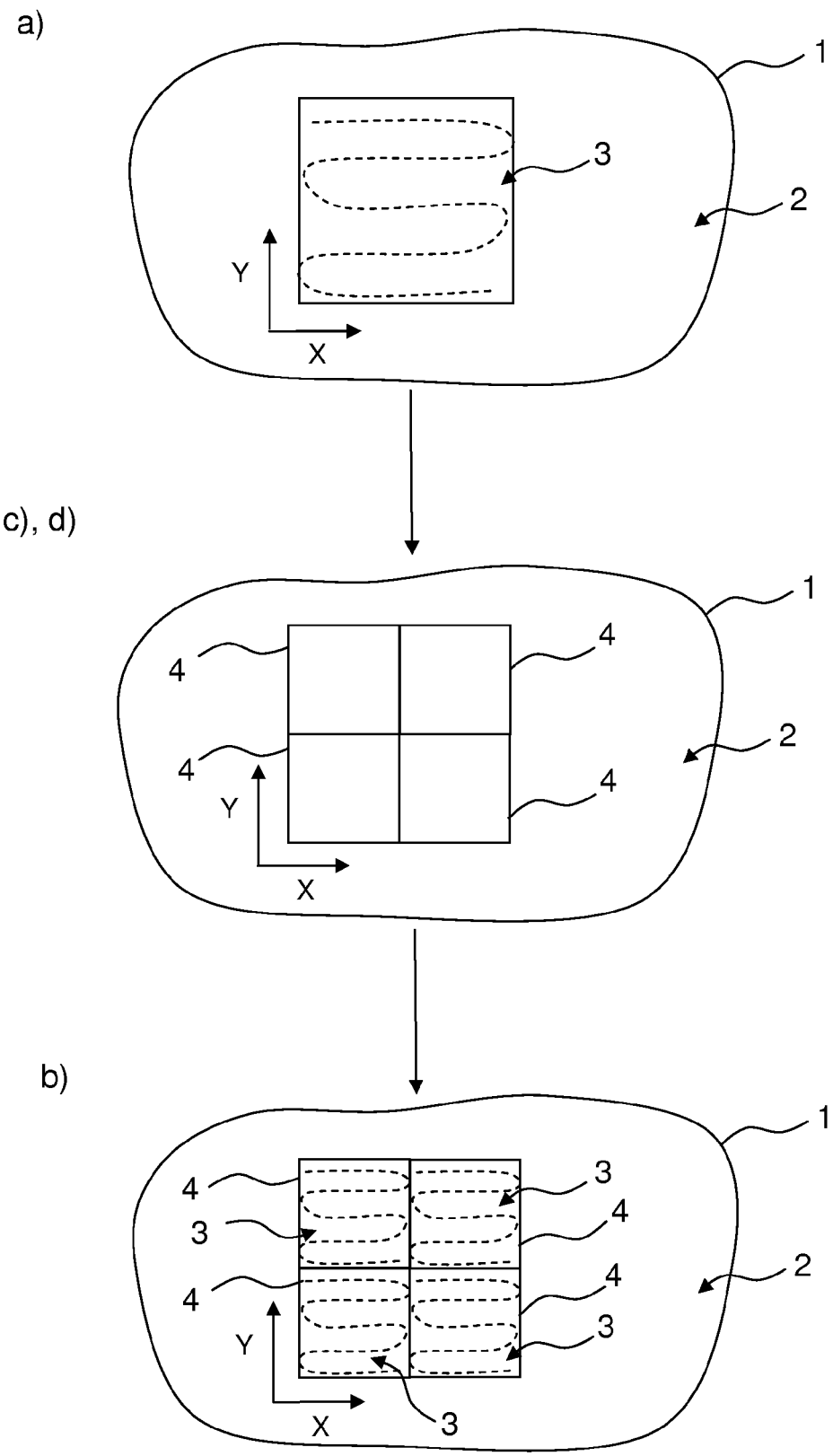
FIG. 3 is a schematic representation of a spectroscopic imaging method, according to another embodiment of the invention.

According to another possible embodiment of the invention, represented in FIG. 3, the third step c) and the fourth step d) are executed before the second step b).

After the first step a) wherein the excitation beam 8 is scanned on a scanned area 3 of the sample surface 2 in two directions X and Y, one applies the third step c) wherein one or several information are selected in the measured energy and the fourth step d) wherein one or more scanned areas 3 are divided in several smaller scanned areas 4, if at least a selected information is detected in the scanned areas 3. In the example of FIG. 3, only one scanned area 3 is scanned and divided in four smaller scanned areas 4.

The second step b) wherein the preceding first step a) is repeated for one or several other scanned areas 3 or smaller scanned areas 4 of the sample surface 2, is then applied. Each smaller scanned area 4 is contiguous to at least one other smaller scanned area 4. The excitation beam 8 is scanned on the four smaller scanned areas 4 of the sample surface 2 in two directions X and Y.

The preceding steps a) to d) are applied to at least a smaller divided scanned area 4. The preceding steps a) to d) can be repeated until the wished resolution is reached.

Thus, if at least a selected information is detected in one of the four smaller scanned areas 4, this one is divided in several other smaller scanned areas 4.

As mentioned in the example of FIG. 2, the scanned areas 3 containing the information characteristic of the one or several elements intended to be localized, can be divided in more or less than four smaller scanned areas 4. The number of divisions can vary during the process.

To conclude, the association of the scanning means with the storage means of the detection means enables to obtain a spectral image such as a Raman image in less than 10 minutes, with a good precision (50 points×50 points). Time required to obtain a spectral image is significantly reduced. The using of scanning means such as galvanometric mirrors permits to reduce the time t required to scan the sample surface. And the using of storage means such as a FPGA module permits to reduce the time required for transferring the data from the detector to the FPGA module and the time required for transferring the data from the FPGA module to the imaging device.

This spectroscopic imaging system is particularly useful when applied to the above described method for localizing an element on a sample surface. One can visualize all the interesting elements of the sample surface on a two-dimensional map, in less than 10 minutes.

The invention claimed is:

1. Spectroscopic imaging method for exploring the surface of a sample comprising a first step a) wherein:
   the sample surface is illuminated with an excitation beam, in order to produce an emitted light,
   the emitted light is collected to form an emitted light beam having an energy,
   the energy of the emitted light beam is measured in order to obtain a spectroscopic image of the sample surface, wherein:
   in the first step a), the excitation beam is scanned on the sample surface in two directions X and Y in order to illuminate a scanned area on the sample surface using scanning means disposed in the optical path of said excitation beam and to measure the energy of the emitted light beam on the scanned area, the energy of the emitted light beam being integrated during the scanning of the excitation beam on the scanned area and a time t, in order to obtain an average spectroscopic image of the scanned area,
   the spectroscopic imaging method further comprises:
   a second step b) wherein the preceding first step a) is repeated for one or several other scanned areas of the sample surface, each scanned area being contiguous to at least one other scanned area,
   a third step c) wherein one or several information are selected in the measured energy,
   a fourth step d) wherein one or more scanned areas are divided in several smaller scanned areas, if at least a selected information is detected in said scanned areas, and
   the preceding steps a) to d) are applied to at least a smaller divided scanned area.

2. Spectroscopic imaging method for exploring the surface of a sample according to claim 1, wherein the energy of the emitted light beam is measured with a detection means comprising several vertical lines of pixels and several horizontal lines of pixels, one of the horizontal lines of pixels being a reading line, each line of pixels including several pixels, and the operation of measurement of the first step a) comprising the steps of:
   e) polarizing the pixels of at least one horizontal line of pixels receiving the integrated energy of the emitted light beam during the time t, generating an amount of electric charges accumulated in each pixel of the at least one horizontal line of pixels,
   f) transferring simultaneously the amount of electric charges of all the pixels of the polarized horizontal line of pixels toward the reading line,
   g) transferring the amount of electric charges of each pixel of the reading line toward an electronic device, said electronic device being able to convert each amount of electric charges into a voltage value, wherein:
   the steps f) and g) are controlled by a storage means comprising a control means, said storage means controlling the transfer rate of the amount of electric charges of the pixels, after the step g) the voltage value of each pixel of the reading line is stored in the storage means, said storage means being able to store an amount of voltage values corresponding to M horizontal lines of pixels, and said stored amount of voltage values corresponding to M horizontal lines of pixels is sent toward an imaging device in order to obtain an average spectroscopic image of the scanned area.

3. Spectroscopic imaging method for exploring the surface of a sample according to claim 1, wherein:
   during the second step b), the first step a) is applied to four scanned areas of the sample surface, said four scanned areas being contiguous, during the fourth step d), at least one of the four scanned areas is divided in four smaller scanned areas if at least a selected information is detected in said at least one of the four scanned areas, and the preceding steps a) to d) are applied to the four smaller divided scanned areas.

4. Spectroscopic imaging method for exploring the surface of a sample according to claim 1, wherein the steps a) to g) are automatically realized.

5. Spectroscopic imaging method for exploring the surface of a sample according to claim 1, wherein during step a), the scanned area is continuously scanned by the excitation beam.

6. Spectroscopic imaging method for exploring the surface of a sample according to claim 1, wherein it is a Raman imaging method for exploring the surface of a sample having Raman property, said excitation beam being a monochromatic light beam able to produce a Raman scattered light, said Raman scattered light being collected to form a Raman scattered light beam having an energy and said energy being filtered and measured in order to obtain a Raman image of the sample surface.

7. Spectroscopic imaging system for exploring the surface of a sample comprising:
   a microscopic or macroscopic device including an objective, a housing including a spectroscope, said spectroscope comprising:
      an excitation source able to generate an excitation beam incident to the sample surface, producing an emitted light,
      collecting means able to collect the emitted light to form an emitted light beam having an energy,
      detection means able to measure the energy of the emitted light beam in order to obtain a spectroscopic image of the sample surface, said detection means comprising at least one line of pixels, and
   scanning means disposed between the objective of the microscopic or macroscopic device and the spectroscope, said scanning means being disposed in the optical path of the excitation beam and being able to scan the sample surface in two directions X and Y in order to illuminate a scanned area on the sample surface, wherein:
      during the scanning of the excitation beam on the scanned area, the energy of the emitted light beam measured on the scanned area is integrated on the pixels of one or more lines of pixels of the detection means, the detection means comprising means for generating average spectral data for said lines of pixels, storage means are connected to the detection means, said average spectral data of each line of pixels being transferred toward the storage means, and said storage means comprising a memory able to store average spectral data of M lines of pixels, and an imaging device is connected to the storage means, said average spectral data of M lines of pixels being sent simultaneously toward said imaging device in order to obtain an average spectroscopic image of the scanned area.

8. Spectroscopic imaging system for exploring the surface of a sample according to claim 7, wherein the storage means comprises control means for controlling the transfer rate of the average spectral data of the pixels of the lines.

9. Spectroscopic imaging system for exploring the surface of a sample according to claim 7, wherein the storage means is a Field Programmable Gate Array module (FPGA).

10. Spectroscopic imaging system for exploring the surface of a sample according to claim 7, wherein the spectroscope is an attachment for the microscopic or macroscopic device.

11. Spectroscopic imaging system for exploring the surface of a sample according to claim 7, wherein the scanning means comprise two galvanometric mirrors.

12. Spectroscopic imaging system for exploring the surface of a sample according to claim 7, wherein it is a Raman imaging system for exploring the surface of a sample having Raman property, said spectroscope being a Raman spectroscope comprising: a monochromatic light source able to illuminate the sample surface with a monochromatic light beam, in order to produce a Raman scattered light, collecting means able to collect the Raman scattered light to form a Raman scattered light beam having an energy, and filtering means and detection means able to filter and measure the energy of the Raman scattered light beam in order to obtain a Raman image of the sample surface.

* * * * *